United States Patent
Kim et al.

(10) Patent No.: US 8,870,567 B2
(45) Date of Patent: Oct. 28, 2014

(54) METHOD FOR DETERMINING POSITION OF ORTHODONTICS MINI-SCREW AND APPARATUS THEREOF

(71) Applicant: Infinitt Healthcare Co., Ltd., Seoul (KR)

(72) Inventors: Jin Kook Kim, Seoul (KR); Jae Il Han, Seoul (KR); Jeong Woon Jeong, Seoul (KR)

(73) Assignee: Infinitt Healthcare Co. Ltd., Seoul (KR)

( * ) Notice: Subject to any disclaimer, the term of this patent is extended or adjusted under 35 U.S.C. 154(b) by 0 days.

(21) Appl. No.: 13/756,185

(22) Filed: Jan. 31, 2013

(65) Prior Publication Data

US 2013/0196280 A1    Aug. 1, 2013

(30) Foreign Application Priority Data

Jan. 31, 2012    (KR) ........................ 10-2012-0009687

(51) Int. Cl.
*A61C 3/00*    (2006.01)
(52) U.S. Cl.
USPC ................................................. 433/24; 433/6
(58) Field of Classification Search
USPC ................ 433/3–24, 72–76, 172–176, 215
See application file for complete search history.

(56) References Cited

U.S. PATENT DOCUMENTS

| | | | |
|---|---|---|---|
| 6,224,373 B1 * | 5/2001 | Lee et al. | 433/172 |
| 2004/0249304 A1 * | 12/2004 | Earthman et al. | 600/553 |
| 2006/0154203 A1 * | 7/2006 | Emanuelli | 433/173 |
| 2013/0244205 A1 * | 9/2013 | Berckmans et al. | 433/173 |

FOREIGN PATENT DOCUMENTS

| | | |
|---|---|---|
| KR | 2002-0086198 | 11/2002 |
| KR | 10-2009-0085619 | 8/2009 |
| KR | 10-0914689 | 8/2009 |
| KR | 10-2009-0119839 | 11/2009 |
| KR | 10-2010-0063909 | 6/2010 |
| KR | 10-2010-0099507 | 9/2010 |
| KR | 10-1097477 | 12/2011 |
| KR | 10-1099732 | 12/2011 |

* cited by examiner

*Primary Examiner* — Yogesh Patel
(74) *Attorney, Agent, or Firm* — Edwards Wildman Palmer LLP; Kongsik Kim (57) ABSTRACT

Disclosed herein are a method and apparatus for determining the location of an orthodontic fastener. In the method, a first location on a tooth and a second location on alveolar bone are set on a patient's medical image. Thereafter, a first rectilinear line including two points, that is, the set first and second locations, is generated. Thereafter, bone density values at the locations of the alveolar bone on the generated first rectilinear line are computed using the medical image. Finally, the location of the alveolar bone at which a first fastener is inserted is determined based on the computed bone density values.

11 Claims, 10 Drawing Sheets

METHOD FOR DETERMINING POSITION OF ORTHODONTICS MINI-SCREW AND APPARATUS THEREOF

CROSS-REFERENCE TO RELATED APPLICATION

This application claims under 35 U.S.C. §119(a) the benefit of Korean Application No. 10-2012-0009687 filed Jan. 31, 2012, which is incorporated herein by reference.

TECHNICAL FIELD

The present invention relates generally to the determination of the location at which an orthodontic fastener will be inserted and, more particularly, to a method and apparatus for determining the location of an orthodontic fastener that are capable of providing the appropriate location at which an orthodontic fastener will be inserted in order to perform orthodontic treatment that uses the orthodontic fastener, such as a mini-screw.

BACKGROUND ART

The life spans of people today are increasing continuously thanks to the improvement of life environments and the development of medical technology. Furthermore, recently, people have emphasized the aspect of the quality of life, in addition to the extension of life-spans. People's interest in the improvement of the quality of life spans a variety of fields. One of these fields is orthodontics.

Orthodontics is directed to recovery from dental parafunctions, such as congenital or acquired damage to or loss of teeth, or the malocclusion of teeth. In particular, in the field of orthodontics, the development and application of new technologies are further promoted by the growth of the aged population that is attributable to the extension of life spans. Furthermore, orthodontics is important not only in the aspect of the recovery of tooth functions, but also in the cosmetic aspect. Many people make investments in dental treatments that are directed to the improvement of their appearances because people's looks are significantly changed simply by reconstructing damaged or lost teeth with prosthetic teeth material or performing the slight straightening of teeth.

Orthodontics may be divided into a plurality of branches. In particular, the branch of interest here is the straightening of teeth. The straightening of teeth is performed in such a way as to gradually move teeth to desired locations by continuously exerting orthodontic force on the teeth over a long period of time. Accordingly, in order to realize the straightening of teeth, one or more tools for exerting orthodontic force are installed in a patient's mouth.

In the past, in order to move a row of teeth, for example, in order to move a protruding mouth backward, a full-arch appliance that embraces the overall dental arch in the form of an arch has been frequently used. This orthodontic tool moves the row of teeth backward chiefly using molar teeth as an anchoring base. However, this anchoring structure makes it difficult to realize desired orthodontic effects because the reaction force of the orthodontic force is exerted on the molar teeth, which are anchoring bases.

Accordingly, recently, thanks to the help of the development of orthodontic technology, a fast orthodontic system, for example, a skeletal anchorage system (SAS), using a dental skeleton (alveolar bone) as an anchoring base was attempted. This fast orthodontic system has the advantage of achieving excellent orthodontic effects within a short period of time compared to the former systems because the fast orthodontic system exerts orthodontic force directly on teeth that have to be straightened.

However, this fast orthodontic system is problematic in that when a fastener is inserted into a gap between the root of a tooth and the alveolar bone, the fastener is removed from the alveolar bone or touches a nerve in the root of the tooth over time because the location at which a fastener, for example, a mini-screw, is determined using a 2D image.

In order to overcome the above problems, a method using cone beam computed tomography (CBCT) and volume data was introduced. However, this method is problematic in that it is not suitable for a user finding the appropriate location at which a fastener, for example, a mini-screw, will be inserted because the user personally analyzes and uses data on an axial, sagittal or coronal 2D screen.

Therefore, there is a need for a method for determining the appropriate location of the alveolar bone at which a fastener will be inserted.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, the present invention has been made keeping in mind the above problems occurring in the prior art, and an object of the present invention is to provide a method and apparatus for determining the location of an orthodontic fastener that are capable of offering a tool that enables the appropriate location of the alveolar bone at which a fastener, for example, a mini-screw, will be inserted to be selected, and thus the appropriate location at which the fastener will be inserted can be accurately determined, thereby reducing the period in which a treatment for inserting the fastener is performed and also increasing the success rate of an orthodontic treatment.

More specifically, in accordance with the present invention, once the direction in which a fastener will be inserted has been set based on a medical image, bone density values of alveolar bone in the set direction are computed using the medical image, and the appropriate location at which the fastener will be inserted is determined based on the computed bone density values, thereby reducing the period in which a treatment for inserting the fastener is performed and also increasing the success rate of an orthodontic treatment.

Another object of the present invention is to provide a method and apparatus for determining the location of an orthodontic fastener that provide a user with information in which user inputs in the direction in which the fastener will be inserted and bone density values in the set direction have been synchronized with each other in a medical image, thereby facilitating the determination of whether a fastener can be inserted, and reducing the time it takes to determine the optimum location at which the fastener will be inserted.

Still another object of the present invention is to provide a method and apparatus for determining the location of an orthodontic fastener that provide an interface that enables the direction in which a fastener will be inserted to be set on a medical image and a location to be set based on bone density values in the corresponding direction, thereby enabling a user to easily set the optimum location at which the fastener will be set.

In accordance with an aspect of the present invention, there is provided a method of determining the location of an orthodontic fastener, including setting a first location on a tooth and a second location on alveolar bone on a patient's medical image; generating a first rectilinear line including two points, that is, the set first and second locations; computing bone density values at locations of the alveolar bone on the generated first rectilinear line using the medical image; and determining a location of the alveolar bone at which a first fastener is inserted based on the computed bone density values.

The method may further include displaying the computed bone density values at the locations of the alveolar bone on a screen on which the medical image is displayed. Displaying the computed bone density values may include, when a third location on the first rectilinear line is selected in response to user input, displaying a bone density value at the selected third location in synchronization of the third location.

In this case, the bone density values at the locations of the alveolar bone may be acquired using the intensity values of the medical image. Computing the bone density values at the locations of the alveolar bone on the generated first rectilinear line may include extracting the intensity values of the medical image in order to acquire the bone density values. Here, the term "bone density values" is not limited to bone density values themselves, but is based on a concept that includes all parameters that fall within the range of values equivalent to bone density values, such as the intensity values of the pixels of a medical image that are extracted to acquire bone density values and that are related to the bone density values.

Determining the location of the alveolar bone may include determining a location having a maximum one of the bone density values to be the location at which the first fastener will be inserted. Determining the location of the alveolar bone comprises determining one of one or more peak locations having maximum ones of the bone density values to be the location at which the first fastener will be inserted while considering at least one of distances to valley locations having minimum bone density values, distances to teeth, and a preset reference bone density value.

The method may further include, if every one of the bone density values on the first rectilinear line is equal to or smaller than a preset reference bone density value, setting a fourth location and a fifth location that are used to generate a second rectilinear line and a third rectilinear line corresponding to the first rectilinear line; generating the second rectilinear line including the first location and the fourth location and the third rectilinear line including the first location and the fifth location; computing bone density values on locations of the alveolar bone on the generated second and third rectilinear lines using the medical image; and determining locations of the alveolar bone at which a second fastener and a third fastener will be inserted based on the computed bone density values on the second rectilinear line and the third rectilinear line.

In accordance with another aspect of the present invention, there is provided an apparatus for determining the location of an orthodontic fastener, including a setting unit configured to set a first location on a tooth and a second location on alveolar bone on a patient's medical image; a generation unit configured to generate a first rectilinear line including two points, that is, the set first and second locations; a computation unit configured to compute bone density values at locations of the alveolar bone on the generated first rectilinear line using the medical image; and a determination unit configured to determine a location of the alveolar bone at which a first fastener is inserted based on the computed bone density values.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Embodiments of the present invention will be described in detail below with reference to the accompanying drawings. In the following description of the embodiments, if it is determined that a detailed description of a related known configuration or function may make the gist of the present invention vague, the detailed description will be omitted. However, the present invention is not limited to the embodiments. Meanwhile, throughout the accompanying drawings, like reference symbols denote like components.

A method and apparatus for determining the location of an orthodontic fastener in accordance with embodiments of the present invention will be described in detail below with reference to FIGS. 1 to 10.

Figure 1:
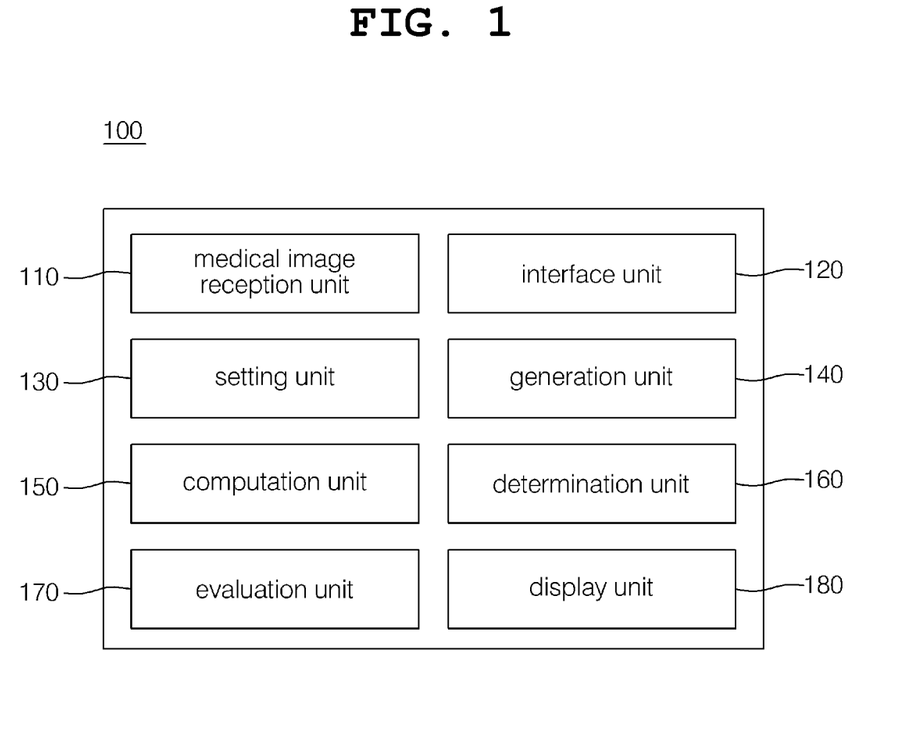
FIG. 1 illustrates the configuration of an apparatus for determining the location of an orthodontic fastener in accordance with an embodiment of the present invention.

FIG. 1 illustrates the configuration of an apparatus 100 for determining the location of an orthodontic fastener in accordance with an embodiment of the present invention.

Referring to FIG. 1, the apparatus 100 for determining the location of an orthodontic fastener includes a medical image reception unit 110, an interface unit 120, a setting unit 130, a generation unit 140, computation unit 150, a determination unit 160, an evaluation unit 170, and a display unit 180.

The medical image reception unit 110 receives a medical image related to a patient's teeth.

Here, the medical image may be an image that is captured by CBCT, an image that is captured by an X-ray, a single image into which a plurality of images is reconstructed, or a three-dimensional (3D) image into which a plurality of images is reconstructed in three dimensions.

Of course, the medical image that is received by the medical image reception unit 110 may be displayed on the screen of the display unit 180.

The interface unit 120 is configured to receive user input related to the determination of the location of a fastener from a user (an orthodontist). The interface unit 120 may receive a user input used to set a first location on a tooth and a second location on alveolar bone on a medical image, and a user input used to move the location of a fastener across a graph of bone density values displayed on the display unit 180.

Of course, the interface unit 120 may perform all the user input-related operations of the present invention as well as the above-described operations.

The setting unit 130 sets a first location on a tooth and a second location on alveolar bone on a patient's medical image, that is, a medical image of teeth, based on the user input that is received through the interface unit 120.

Here, the first location may be placed on a part of a tooth or on a part of a structure configured to connect the teeth in order to straighten the teeth or a structure formed on a tooth, whereas the second location may be set at a location in a direction that enables orthodontic force to be exerted with respect to the first location.

Figure 2:
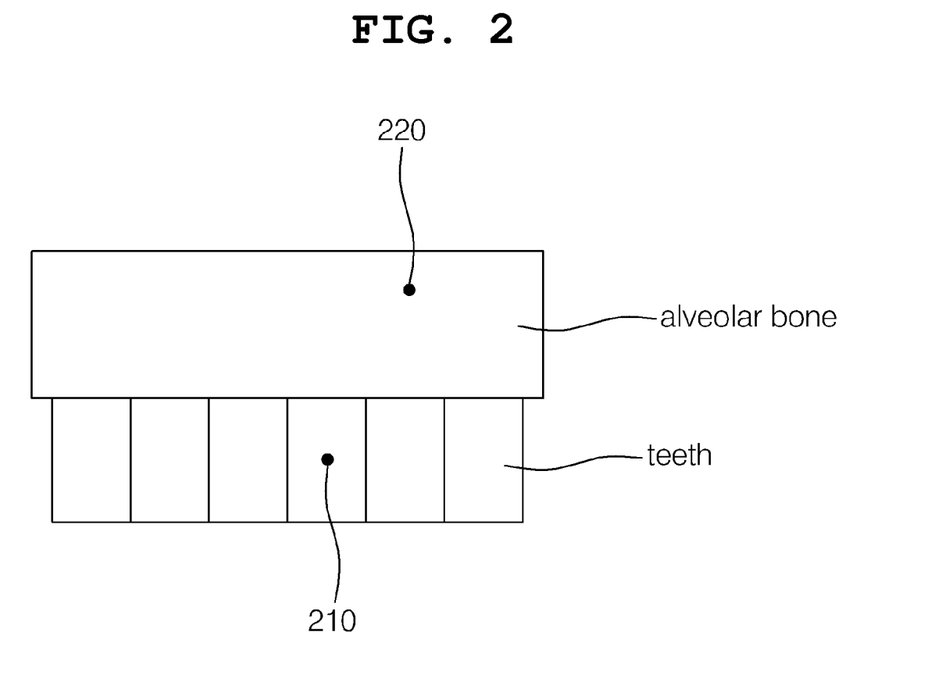
FIG. 2 is a schematic diagram illustrating an example of setting a first location on a tooth and a second location on alveolar bone that are used to determine the location at which a fastener will be inserted, in accordance with an embodiment of the present invention.

For example, as shown in FIG. 2, which is a schematic diagram of teeth and alveolar bone, the first and second locations 210 and 220 are set on a tooth and alveolar bone, respectively, and are set on a patient's teeth image that is displayed on the screen through the interface unit 120. The reason why the second location 220 is illustrated as being offset from the first location 210 to the right in FIG. 2 is that orthodontic force is intended to be applied to the teeth to the right or to the upper right.

Of course, although the schematic diagram of the teeth and alveolar bone is illustrated in FIG. 2, it will be apparent that in practice, the first location and the second location are set on a patient's teeth image that is captured by a medical imaging device. The following description will be given using schematic diagrams, rather than actual medical images of the teeth and alveolar bone, for ease of description.

The generation unit 140 generates a rectilinear line including the two points, that is, the first and second locations, of the medical teeth image that are set by the setting unit 130.

That is, the generation unit 140 generates a line on alveolar bone that is used to determine the location at which a fastener, for example, a mini-screw, will be inserted.

Figure 3:
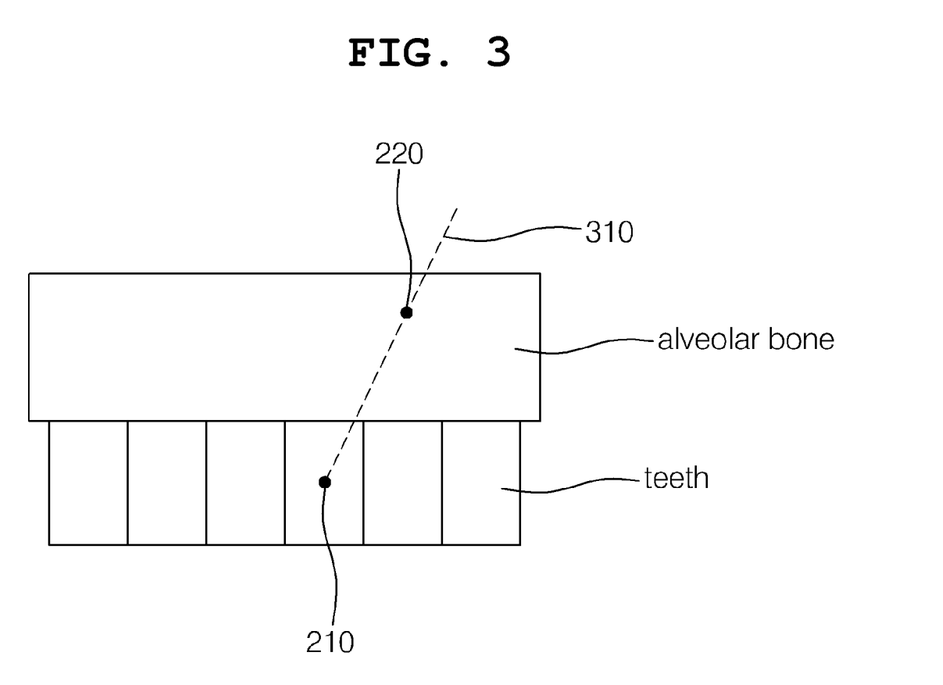
FIG. 3 is a schematic diagram illustrating an example of generating a rectilinear line using the first and second locations of FIG. 2 in accordance with an embodiment of the present invention.

For example, the generation unit 140 generates a rectilinear line 310 including the first and second locations 210 and 220 illustrated in FIG. 2, and then displays the generated rectilinear line 310 on the medical teeth image, as illustrated in the schematic diagram of FIG. 3.

Here, the rectilinear line 310 is preferably a rectilinear line that extends from the first location 210 to the second location 220. Although the generated rectilinear line 310 is illustrated as a dotted line, the generated rectilinear line 310 is not limited thereto, but may be visualized in various forms and provided to the user.

Furthermore, the generation unit 140 may generate a virtual shape of a fastener, and provide it onto the generated rectilinear line. The virtual shape of a fastener may vary depending on the type of fastener that is selected by the user.

Figure 4:
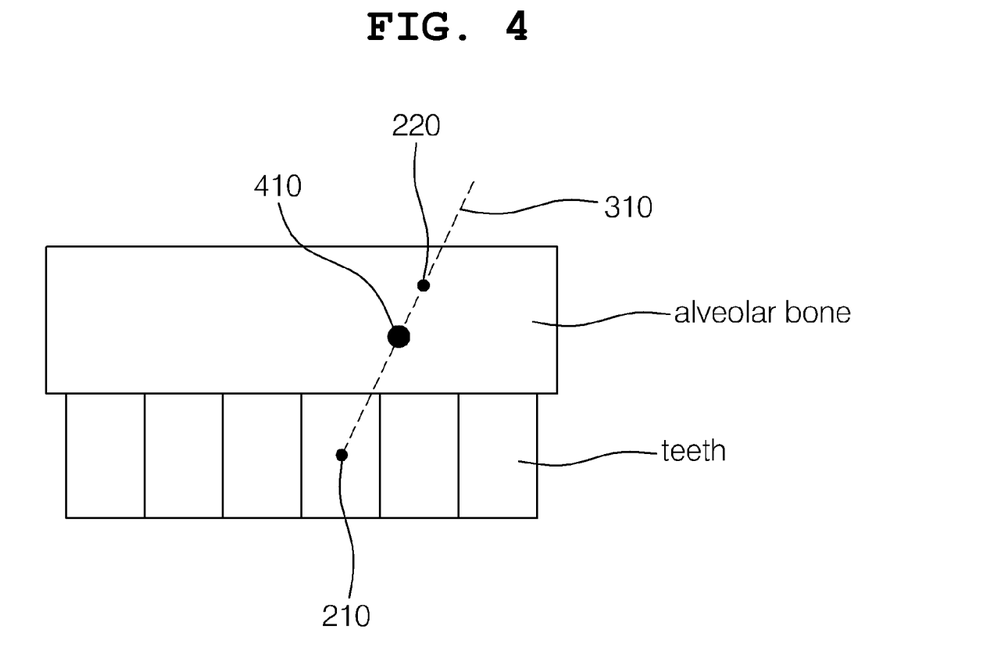
FIG. 4 is a schematic diagram illustrating an example of moving the location of a fastener along the rectilinear line of FIG. 3 in accordance with an embodiment of the present invention.

For example, as shown in the schematic diagram of FIG. 4, the generation unit 140 virtually displays a virtual shape 410 of a fastener of a selected type on one point of a rectilinear line 310 when the type of fastener is selected, and thus the location of the fastener may be moved.

In this case, the fastener 410 can be moved only along the rectilinear line 310. The movement can be performed only in the arrow direction of FIG. 4. If necessary, the radius of the movement may be limited. A setting may be made so that the movement is performed only along alveolar bone. Of course, in order to enable the movement to be performed only along alveolar bone, image processing is performed to recognize the teeth and alveolar bone. The radius of the movement may be limited to recognized alveolar bone when the alveolar bone is recognized by the image processing.

The computation unit 150 computes bone density values at locations of the alveolar bone along the rectilinear line generated by the generation unit 140, using the medical teeth image that is displayed on the display unit 180.

Here, a method of computing bone density values using a medical teeth image may be, for example, a method using the pixel values of a medical teeth image. Of course, the method of computing bone density values in accordance with the present invention may be any one of methods that are capable of computing bone density values on a medical image. Here, the term "bone density values" is not limited to bone density values themselves, but is based on a concept that includes all parameters that fall within the range of values equivalent to bone density values, such as the intensity values of the pixels of a medical image that are extracted to acquire bone density values and that are related to the bone density values.

The bone density values at the locations on the rectilinear line, which are computed by the computation unit 150, may be visually displayed on the screen.

Figure 5:
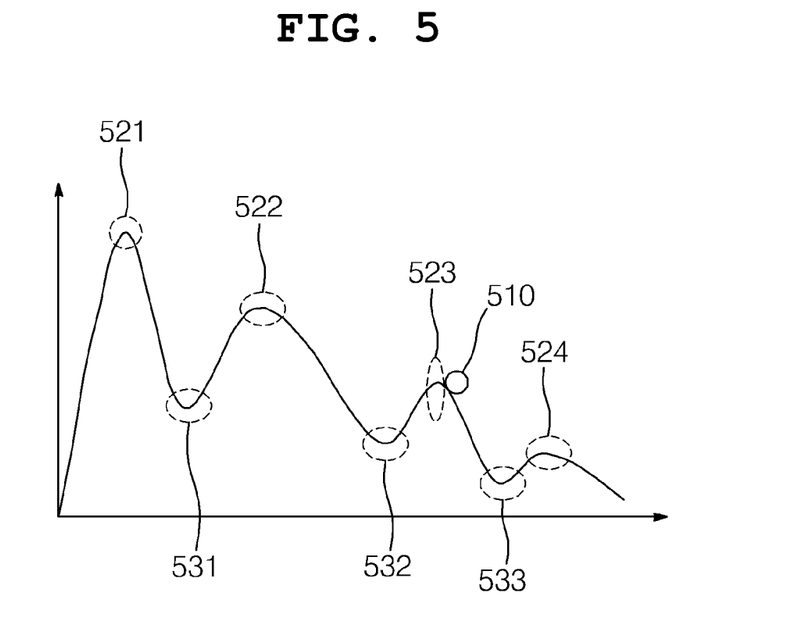
FIG. 5 is a graph illustrating bone density values at locations on the rectilinear line of FIG. 3.

Here, the bone density values that are computed by the computation unit 150 may be displayed in the form of a graph of bone density values based on the locations of the alveolar bone, along with the medical image, as illustrated in the example of FIG. 5. The bone density values may be displayed in the form of a table of locations and bone density values at regular intervals along the rectilinear line. When the bone density values are displayed in the form of a table, it is preferable to display the bone density values as being matched to the corresponding locations along the rectilinear line. Furthermore, when a location on the rectilinear line is selected, a bone density value that belongs to the bone density values displayed in the form of a table and that corresponds to the corresponding location may be visualized so that it can be distinct from other values. In contrast, when a specific bone density value is selected from the table, a location on the rectilinear line corresponding to the specific bone density value may be visualized so that it can be distinct from other locations.

Of course, when the bone density values are displayed in the form of a graph, as illustrated in FIG. 5, and a virtual fastener moves along the rectilinear line on the medical image in synchronization with the rectilinear line, a movement may be made to a bone density value at a corresponding location in the graph. Alternatively, when a movement is made across the graph of bone density values, the fastener may be moved to a corresponding location on the rectilinear line.

Here, in the graph shown in FIG. 5, location movement means 510 indicative of the location of the virtual fastener on the graph may be visualized. The location movement means 510 may be moved by a user input, for example, a press of a directional key or a mouse input, through the interface unit 120.

Additionally, the apparatus in accordance with the present invention may display at least one location having an optimum bone density value, that is, at least one location on the rectilinear line, together with the bone density value, based on the bone density values that are computed by the computation unit 150.

Figure 6:
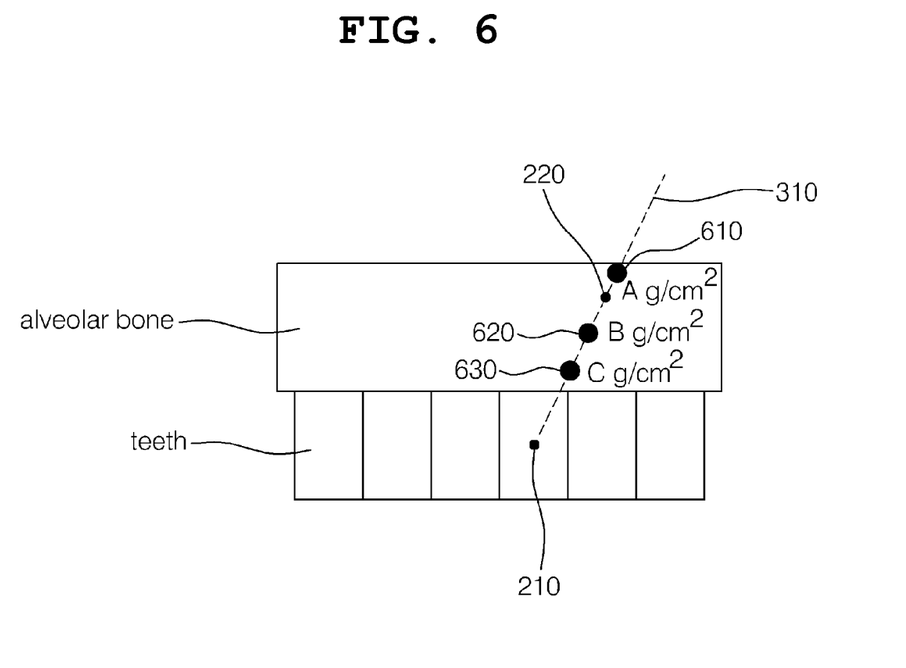
FIG. 6 is a schematic diagram illustrating an example of automatically displaying the appropriate locations of a fastener along the rectilinear line of FIG. 3 in accordance with an embodiment of the present invention.

For example, as illustrated in the example of FIG. 6, bone density values A, B, and C g/cm$^2$ may be displayed at locations 610 to 630 that correspond to bone density values that are selected from among the bone density values, computed along the rectilinear line on the medical image by the computation unit 150, pursuant to preset criteria. In some cases, these bone density values are displayed along with FIG. 5, and thus the optimum locations are displayed both on the rectilinear line and on the graph of bone density values, thereby aiding in determining an optimum location.

In this case, priorities may be assigned to the one or more optimum locations illustrated in FIG. 6, and then priority information may be provided to a user.

The determination unit 160 determines the location of the fastener to be inserted into the alveolar bone based on the bone density values that are computed by the computation unit 150.

In this case, the determination unit 160 may determine that the location on the rectilinear line that has the largest of the bone density values computed by the computation unit 150 is the location at which the fastener will be inserted. For example, the determination unit 160 may determine that a first peak location 521 having the largest of the bone density values illustrated in FIG. 5 is the location at which the fastener will be inserted.

Here, the determination unit 160 may determine one of one or more peak locations having the maximum ones of the bone density values computed by the computation unit 150 to be the location at which the fastener will be located while considering at least one of the distances to valley locations having minimum bone density values, the distances to the teeth, and the preset reference bone density value. For example, the determination unit 160 considers the distances to valley locations 531 to 533, that is, the distances to locations having low bone densities, the distances to the teeth representative of whether a corresponding peak location is a location that is close to a tooth or a location that is far from a tooth, and/or the reference bone density value that is a criterion for the insertion of a fastener, at peak locations 521 to 524 having maximum ones of the bone density values, as shown in FIG. 5. If the first maximum value 521 location does not meet the above-described at least one condition, it is unsuitable for the insertion of the fastener, although it has the maximum bone density value. Accordingly, one of the other peak locations 522 to 524 may be determined to be the location at which the fastener will be inserted.

The evaluation unit 170 evaluates whether each of the bone density values on the rectilinear line that is generated by the generation unit 140 is larger than a preset first reference bone density value.

Here, the evaluation unit 170 is configured to determine that each of the bone density values on the rectilinear line set by the user is larger than the first reference bone density value that is suitable for the insertion of the fastener. If every one of the bone density values on the rectilinear line is equal to or smaller than the first reference bone density value, it is determined that the part of the alveolar bone located on the corresponding rectilinear line is not unsuitable for the insertion of the fastener.

Accordingly, if, as a result of the determination of the evaluation unit 170, it is determined that every one of the bone density values of the part of the alveolar bone located on the rectilinear line is equal to or smaller than the first reference bone density value, the setting unit 130 sets fourth and fifth locations on the alveolar bone in order to generate two rectilinear lines, that is, second and third rectilinear lines, that correspond to the rectilinear line that is generated based on the first and second locations.

Here, the second rectilinear line may be a rectilinear line including two points, that is, the first and fourth locations, and the third rectilinear line may be a rectilinear line including two points, that is, the first and fifth locations.

Here, it is preferred that the second and third rectilinear lines be generated so that the direction of the vector sum of the two rectilinear lines is conformable or close to the direction of the vector of the rectilinear line that is generated based on the first and second locations.

Furthermore, the generation unit 140 generates the second and third rectilinear lines using the fourth and fifth locations set by the setting unit 130, the computation unit 150 computes bone density values at the locations of alveolar bone on each of the second and third rectilinear lines using a medical image, and the determination unit 160 determines the location of the alveolar bone at which each of second and third fasteners will be inserted, based on the bone density values on each of the second and third rectilinear lines.

The determination unit 160 may determine the locations at which the second and third fasteners will be inserted as described above, and the evaluation unit 170 evaluates whether the second and third fasteners can be inserted using the bone density values on the second and third rectilinear lines.

In this case, a bone density value that is used by the evaluation unit 170 in order to evaluate whether the two fasteners can be inserted may be identical to or different from that that is used to determine whether a single fastener can be inserted.

Figure 7:
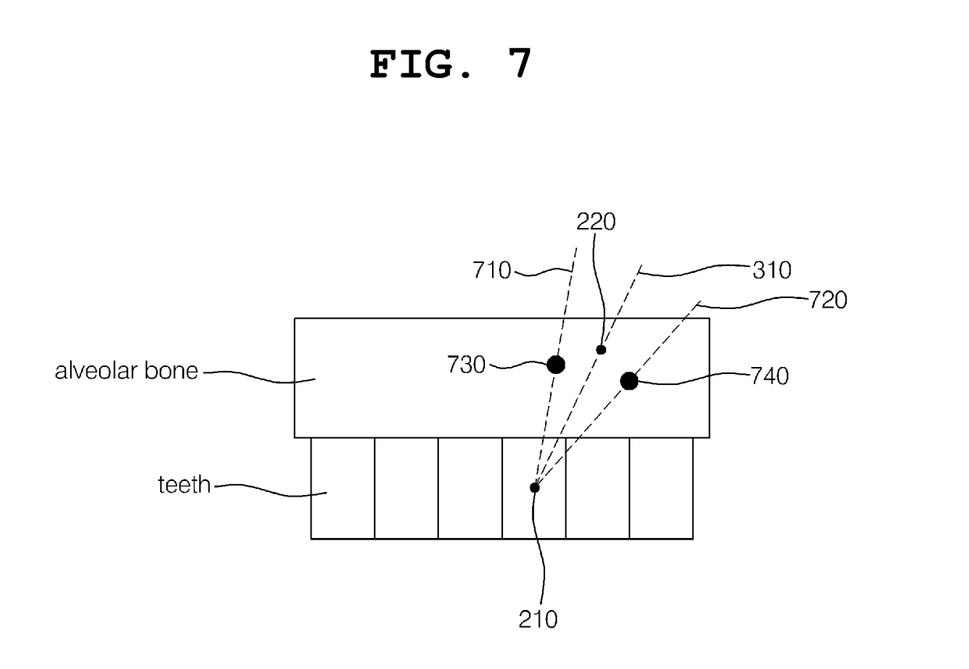
FIG. 7 is a schematic diagram illustrating an example of determining the locations of two fasteners if bone density values on the rectilinear line of FIG. 3 are unsuitable, in accordance with an embodiment of the present invention.

For example, as illustrated in the schematic diagram of FIG. 7, if every one of the bone density values of alveolar bone on the rectilinear line 310 is equal to or smaller than the first reference bone density value, a fourth location (not shown) and a fifth location (not shown) that are used to generate two rectilinear lines 710 and 720 that enable orthodontic force to be exerted on a tooth in a direction toward the rectilinear line 310 are set, and the location on the second rectilinear line 710 at which the second fastener 730 will be inserted and the location on the third rectilinear line 720 at which the third fastener 740 will be inserted based on bone density values on the two generated rectilinear lines 710 and 720. In this case, the orthodontic force may be exerted in the direction toward the rectilinear line 310.

The display unit 180 displays a medical image, displays a graph or a table related to bone density values, and displays all display-related data on a screen such as data related to an interfacing task for setting locations in order to generate a rectilinear line.

In particular, the display unit 180 may display bone density values at locations of alveolar bone on a rectilinear line together with a medical image, and may display a bone density value at a selected third location in synchronization with the third location if the third location at which the fastener will be inserted is selected on a rectilinear line including the first and second locations in response to user input. Since a detailed description thereof has been already given in conjunction with FIG. 5, it is omitted here.

As described above, the apparatus for determining the location of an orthodontic fastener in accordance with this embodiment of the present invention determines the appropriate location of alveolar bone at which an orthodontic fastener will be inserted based on bone density values of the alveolar bone in a direction that is set by a user, and the optimum location of the alveolar bone at which the fastener will be inserted can be determined, thereby reducing the period in which a treatment for inserting the fastener is performed and also increasing the success rate of an orthodontic treatment.

Furthermore, the apparatus for determining the location of an orthodontic fastener in accordance with this embodiment of the present invention provides bone density values in the direction in which a fastener will be inserted on a medical image in synchronization with the medical image, thereby enabling a user to easily determine the optimum location at which the fastener will be inserted and also facilitating the determination of whether the fastener can be inserted.

Meanwhile, the apparatus for determining the location of an orthodontic fastener in accordance with this embodiment of the present invention may further perform the process of, once the first and second locations have been determined and a rectilinear line that connects the first and second locations has been determined, displaying the determined rectilinear line on a medical image. Here, the displayed medical image may be a 3D reconstructed medical image, or a multi-planar reconstructed (MPR) image including the determined rectilinear line.

In this case, the 3D reconstructed medical image may be displayed to illustrate whether the determined rectilinear line interferes with the other portion of the teeth or gums. The MPR image may be generated based on a plane including the determined rectilinear line. The reference surface based on which the MPR image is generated may be defined as a plane that includes the determined rectilinear line and that extends in the direction in an orthodontic fastener that will be inserted at a location of alveolar bone included in the rectilinear line is fastened.

In this case, the MPR image may be generated using a Maximum Intensity Projection (MIP) method that defines a volume of predetermined thickness including a reference surface and selects a maximum intensity value within the defined volume as a representative value for the reference surface of the volume. Alternatively, the MPR image may be generated using a minimum intensity projection (minIP) method that selects a minimum intensity value within a defined volume as a representative value for the reference surface of the volume. Alternatively, the MPR image may be generated using an X-ray sum technique that sums the intensity values of a medical image within a defined volume and then performs projection onto the reference surface of the volume.

Furthermore, the apparatus for determining the location of an orthodontic fastener may visualize and display the first and second locations set by the user, the third location at which the orthodontic fastener will be inserted, and/or a location that is moved along the rectilinear line on the medical image, such as a 3D image, or an MPR image. The apparatus for determining the location of an orthodontic fastener may display the locations in synchronization with the bone density value graph of FIG. 5. Of course, when the apparatus for determining the location of an orthodontic fastener displays the locations in synchronization with the bone density value graph, it may display the first and second locations on the bone density value graph, and may additionally display information, such as the distance and the difference in bone density value between a moved location and the first location and the distance and the difference in bone density value between the moved location and the second location.

Moreover, when a third location on a rectilinear line at which the orthodontic fastener will be inserted is selected by the user, the apparatus for determining the location of an orthodontic fastener may check whether the first location on a tooth and the determined third location are connected with a rectilinear line. If the first and third locations are not connected with a rectilinear line, the apparatus for determining the location of an orthodontic fastener may provide information about the heights to which the first and/or third locations should be raised in order to connect the locations with a rectilinear line. For example, whether the two locations can be connected with a rectilinear line may be determined using the information of plane medical images of the relationship between the first and third locations, for example, information about the heights of the first and third locations and information about the difference in height between the first and third locations. If it is determined based on the above information that the two locations cannot be connected with a rectilinear line, information about the heights to which the first and/or third locations should be raised may be provided to the user.

Furthermore, when the user changes a location on the rectilinear line with a user input, such as a mouse input, in order to determine the third location at which the orthodontic fastener will be inserted after the first and second locations have been set, a rectilinear line from the first location to the currently changed location is displayed on at least one medical image, such as a 2D image, a 3D image, or an MPR. Information about whether the rectilinear line from the first location to the currently changed location interferes with the teeth or the gums may be displayed along with the medical image.

Figure 8:
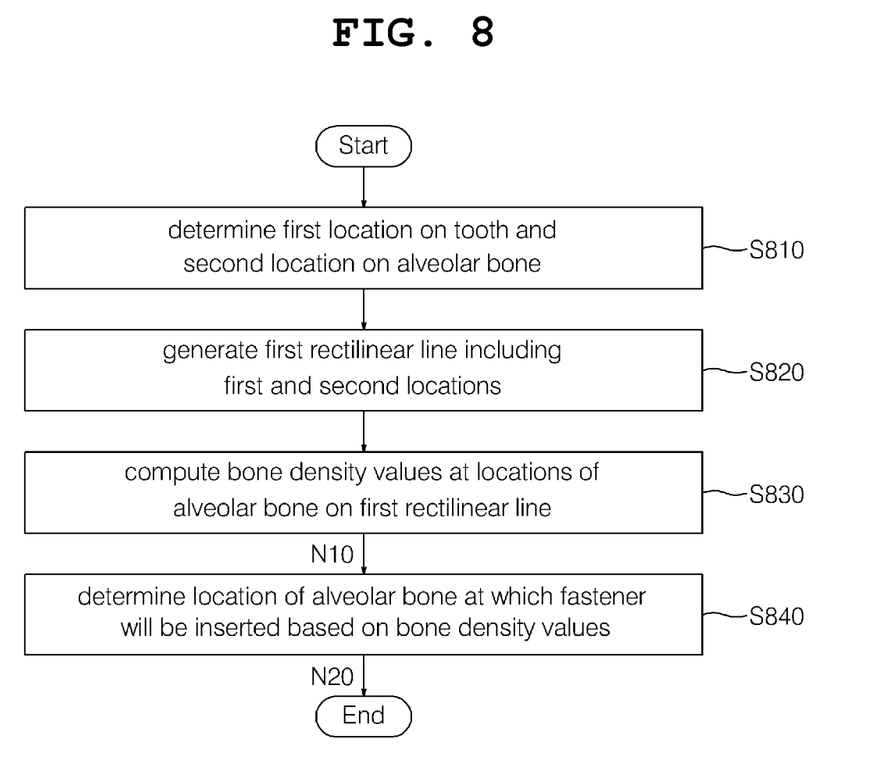
FIG. 8 is an operating flowchart illustrating a method of determining the location of an orthodontic fastener in accordance with an embodiment of the present invention.

FIG. 8 is an operating flowchart illustrating a method of determining the location of an orthodontic fastener in accordance with an embodiment of the present invention.

Referring to FIG. 8, in the method of determining the location of an orthodontic fastener in accordance with this embodiment of the present invention, a first location on a tooth and a second location on alveolar bone are set on a patient's teeth image at step S810.

Here, the first location may be placed on part of a tooth or on part of a structure configured to connect the teeth in order to straighten the teeth or a structure formed on a tooth, whereas the second location may be set at a location in a direction that enables orthodontic force to be exerted with respect to the first location.

Once the first and second locations have been set, a first rectilinear line including two points, that is, the first and second locations is set and bone density values at the locations of the alveolar bone on the generated first rectilinear line are computed at steps S820 and S830

Here, the bone density values on the first rectilinear line may be computed using the pixel values of the medical image across which the first rectilinear line is located. If there is a plurality of medical images, the bone density values may be computed using the pixel values of the plurality of medical images at corresponding locations. Alternatively, bone density values may be computed using any one of other various methods.

Once the bone density values at the locations of the alveolar bone on the first rectilinear line have been computed, the location on the alveolar bone at which the fastener will be inserted is determined based on the computed bone density values at step S840.

Here, the location on the alveolar bone at which the fastener will be inserted may be determined by the user. The location on the alveolar bone that is determined by the user may be a location that has the highest of the bone density values on the first rectilinear line, or a location that is determined by considering various conditions.

Here, the location on the alveolar bone that is determined by considering various conditions may be any one of one or more peak locations that have the maximum ones of the bone density values. The conditions that may be considered in order to determine the location at which the fastener will be inserted may be one or more of the distances to valley locations having minimum bone density values, the distances to the teeth, and a preset reference bone density value. Of course, one or more other conditions that can be considered in order to determine the location at which the fastener will be inserted may be considered additionally or instead.

The method of determining the location of a fastener in accordance with this embodiment of the present invention may visualize and display bone density values together with a medical image in order to enable a user to easily determine the location of the fastener, and, if the bone density values on the first rectilinear line are unsuitable, may use two other rectilinear lines in order to exert orthodontic force toward the first rectilinear line. This will be described with reference to FIG. 9.

Figure 9:
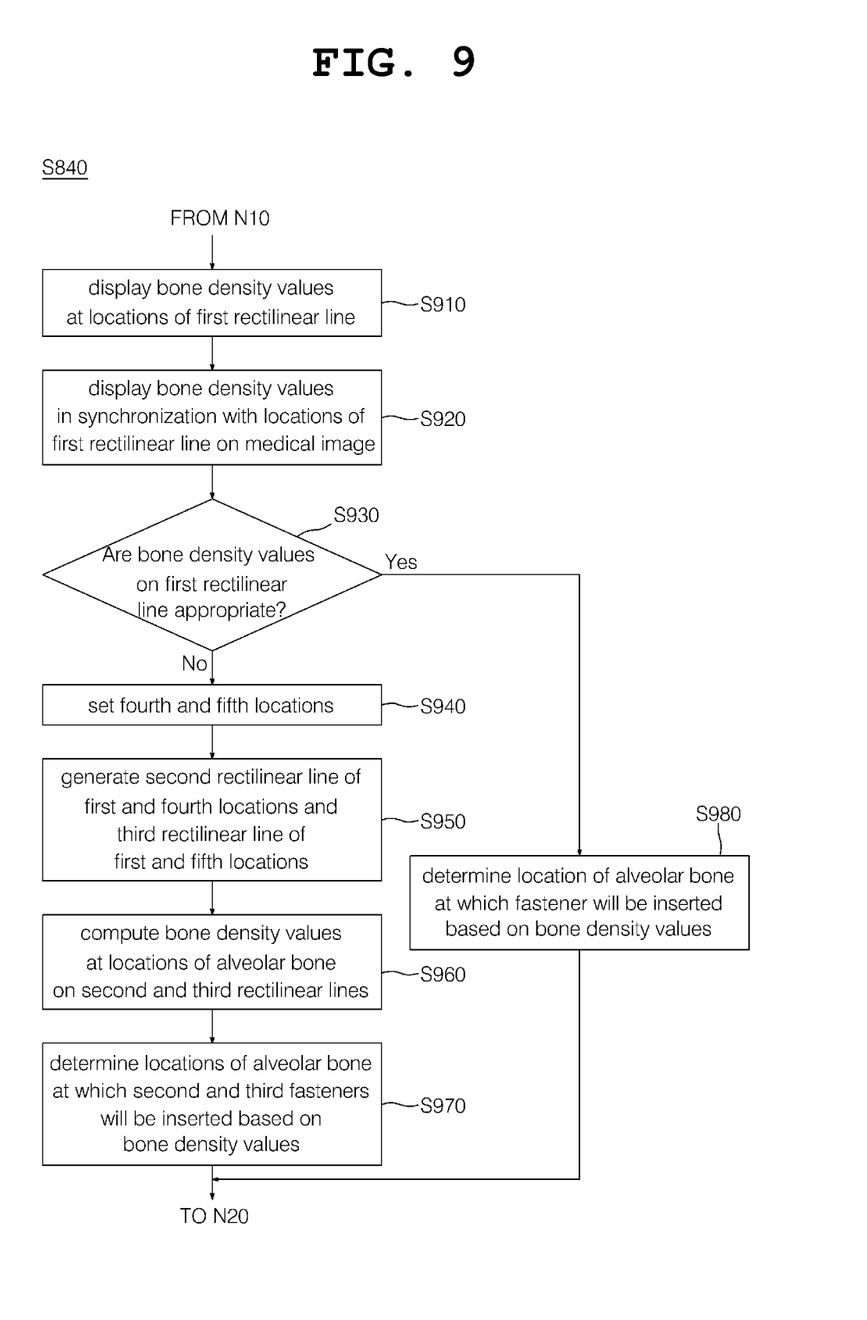
FIG. 9 is an operating flowchart illustrating step S840 of FIG. 8 in accordance with an embodiment of the present invention.

FIG. 9 is an operating flowchart illustrating step S840 of FIG. 8 in accordance with an embodiment of the present invention.

Referring to FIG. 9, at step S840 of determining the location, the bone density values computed at step S830 are displayed at locations on the first rectilinear line and the computed bone density values are displayed in synchronization with the locations on the first rectilinear line on the medical image at steps S910 and S920.

Here, the bone density values at the locations of the alveolar bone on the first rectilinear line may be displayed in the form of a graph along with the medical image, may be displayed in the form of a table in which the locations on the first rectilinear line have been matched to the bone density values, or may be displayed at regular intervals on the first rectilinear line. Furthermore, if necessary, in order to aid in determining an optimum insertion location, one or more locations any one of which may be determined to be the optimum insertion location and bone density values at the locations may be visualized and displayed.

The synchronization of the bone density values with the corresponding locations at step S920 may be performed using any one of methods capable of synchronizing two types of information with each other. When one of the two types of information that have been synchronized with each other is changed, the other is also changed. For example, when a location is moved across a bone density value graph, the location of a virtual fastener is moved along the first rectilinear line on the medical image.

At step S930, it is determined whether there is a bone density value suitable for the insertion of the fastener among the bone density values of the alveolar bone on the first rectilinear line that are computed at step S920.

In this case, whether there is a bone density value larger than a reference bone density value may be determined by comparing the bone density values of the alveolar bone on the first rectilinear line with the preset reference bone density value.

If, as a result of the determination at step S930, a bone density value on the first rectilinear line is suitable for the insertion of the fastener, that is, there is a value larger than the reference bone density value among the bone density values on the first rectilinear line, the location on the alveolar bone at which the fastener will be inserted is determined based on the computed bone density values on the first rectilinear line at step S980.

In contrast, if, as a result of the determination at step S930, every bone density value on the first rectilinear line is unsuitable, that is, every bone density value on the first rectilinear line is equal to or smaller than the reference bone density value, fourth and fifth locations are set on the alveolar bone in order to generate second and third rectilinear lines that enables orthodontic force to be exerted toward the first rectilinear line at step S940.

Once the fourth and fifth locations have been set, the second rectilinear line including two points, that is, the first location set at step S810 and the fourth location, and the third rectilinear line including two points, that is, the first location and the fifth location, are generated at step S950.

Once the second and third rectilinear lines have been generated, bone density values on the locations of the alveolar bone on the generated second and third rectilinear lines are computed, the location at which the second fastener will be inserted is determined based on the bone density values computed with respect to the second rectilinear line, and the location at which the third fastener will be inserted is computed based on the bone density values computed with respect to the third rectilinear line at steps S960 and S970.

That is, if it is difficult to straighten a tooth using a single fastener, orthodontic force is caused to be exerted toward the first rectilinear line by two fasteners.

Figure 10:
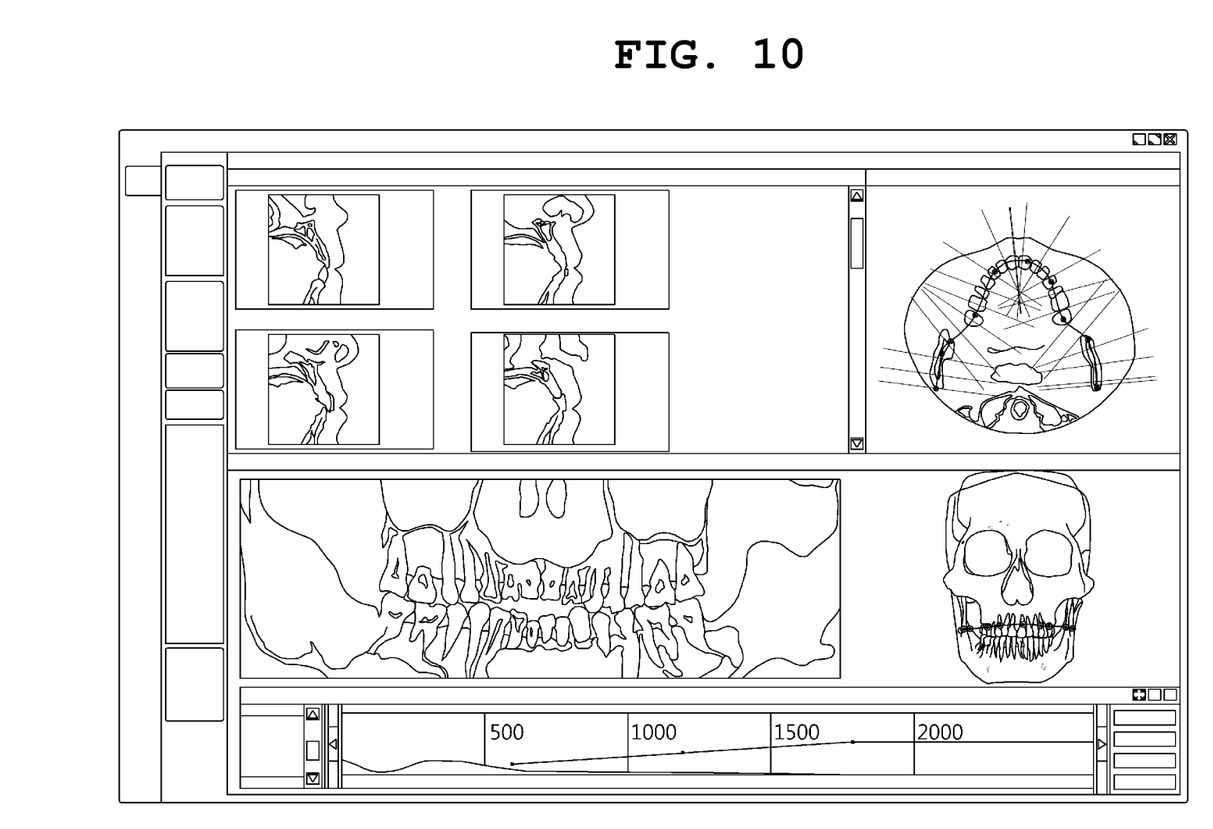
FIG. 10 shows examples of displaying medical images of orthodontic fasteners whose locations have been determined, the teeth and the gums in accordance with various embodiments of the present invention.

FIG. 10 shows examples of displaying medical images of orthodontic fasteners whose locations have been determined, the teeth and the gums in accordance with various embodiments of the present invention.

Referring to FIG. 10, a sagittal plane image is shown on the upper left side thereof, a multi-planar reconstructed (MPR) image is shown on the upper right side thereof, a panoramic reconstructed image is shown on the lower left side thereof, and a 3D volume reconstructed image is shown on the lower right side thereof.

An orthodontic fastener the location of which has been determined in accordance with the present invention is visualized and displayed as various medical images, as shown in FIG. 10, with the result that a user (orthodontist) can previously evaluate whether an orthodontic fastener, such as a mini-screw, can achieve predetermined orthodontic effects at a currently determined location without causing interference with the gums or other teeth.

The method of determining the location of an orthodontic fastener in accordance with the embodiment of the present invention may be implemented in the form of program instructions that can be executed by a variety of computer means, and may be stored in a computer-readable storage medium. The computer-readable storage medium may include program instructions, a data file, and a data structure solely or in combination. The program instructions that are stored in the medium may be designed and constructed particularly for the present invention, or may be known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code that is constructed by a compiler but also high-level language code that can be executed by a computer using an interpreter or the like. The above-described hardware components may be configured to act as one or more software modules that perform the operation of the present invention, and vice versa.

In accordance with the present invention, the appropriate location on alveolar bone at which an orthodontic fastener will be inserted based on the bone density values of alveolar bone set in a direction set by a user, and thus the optimum location on the alveolar bone can be determined, thereby reducing the period in which a treatment for inserting the fastener is performed and also increasing the success rate of an orthodontic treatment.

Furthermore, in accordance with the present invention, the direction in which a fastener will be inserted is set on a medical image, bone density values in the set direction are provided in synchronization with the medical image, and the direction in which the fastener will be inserted and the bone density values are provided through a user interface, thereby enabling a user to easily determine an optimum location and facilitating the determination of whether the fastener can be inserted.

More specifically, in accordance with the present invention, when the direction in which a fastener will be inserted is set on a medical image, bone density values are computed for a rectilinear line in the direction set on the medical image, and the computed bone density values can be displayed in synchronization with locations on the rectilinear line. Accordingly, when the location of a virtual fastener on the rectilinear line is changed, a value or a location on a graph of bone density values that corresponds to the location of the virtual fastener is displayed. In contrast, when a location on a graph is changed, the changed location of the fastener on the rectilinear line can be automatically displayed. As a result, an appropriate location on alveolar bone that has an appropriate bone density value that is suitable for the insertion of the fastener can be determined, thereby ensuring the success of the insertion of the fastener and the safety of a patient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of determining a location of an orthodontic fastener, comprising:
   setting on a patient's medical image, by a processor within a computer, a first location on a tooth and a second location on alveolar bone;
   generating, by the processor within the computer, a first rectilinear line including two points, that is, the set first and second locations;
   computing, by the processor within the computer, bone density values at locations of the alveolar bone on the generated first rectilinear line using the medical image; and
   determining, by the processor within the computer, a location of the alveolar bone on the first rectilinear line at which a first fastener is to be inserted based on the computed bone density values.

2. The method of claim 1, further comprising displaying on a screen, by the processor, the computed bone density values at the locations of the alveolar bone on a screen on which the medical image is displayed.

3. The method of claim 2, wherein displaying further comprises, when a third location on the first rectilinear line is selected in response to user input, the processor displays a bone density value at the selected third location in synchronization of the third location.

4. The method of claim 1, wherein determining further comprises determining a location having a maximum one of the bone density values to be the location at which the first fastener is to be inserted.

5. The method of claim 1, wherein determining further comprises determining one of one or more peak locations having maximum ones of the bone density values to be the location at which the first fastener will be inserted based on at least one selected from a group consisting of: distances to valley locations having minimum bone density values, distances to teeth, and a preset reference bone density value.

6. The method of claim 1, further comprising:
   if every one of the bone density values on the first rectilinear line is equal to or smaller than a preset reference bone density value, setting, by the processor, a fourth location and a fifth location that are used to generate a second rectilinear line and a third rectilinear line respectively;
   generating, by the processor, the second rectilinear line including the first location and the fourth location and the third rectilinear line including the first location and the fifth location;
   computing, by the processor, bone density values on locations of the alveolar bone on the generated second and third rectilinear lines using the medical image; and
   determining, by the processor, locations of the alveolar bone at which a second fastener and a third fastener to be inserted based on the computed bone density values on the second rectilinear line and the third rectilinear line.

7. A non-transitory computer-readable medium containing executable program instructions executed by a processor that stores a program for executing a method of determining a location of an orthodontic fastener, comprising:
   program instructions that set on a patient's medical image a first location on a tooth and a second location on alveolar bone;
   program instructions that generate a first rectilinear line including two points, that is, the set first and second locations;
   program instructions that compute bone density values at locations of the alveolar bone on the generated first rectilinear line using the medical image; and
   program instructions that determine a location of the alveolar bone at which a first fastener is inserted based on the computed bone density values.

8. A computer for determining a location of an orthodontic fastener, comprising:
   a processor configured to:
   set on a patient's medical image a first location on a tooth and a second location on alveolar bone;
   generate a first rectilinear line including two points, that is, the set first and second locations;
   compute bone density values at locations of the alveolar bone on the generated first rectilinear line using the medical image; and
   determine a location of the alveolar bone at which a first fastener is inserted based on the computed bone density values.

9. The apparatus of claim 8, wherein the processor further configured to:
   display the computed bone density values at the locations of the alveolar bone on a screen on which the medical image is display, and to, when a third location on the first rectilinear line is selected in response to user input, display a bone density value at the selected third location in synchronization of the third location.

10. The apparatus of claim 8, wherein the processor determines one of one or more peak locations having maximum ones of the bone density values to be the location at which the first fastener to be inserted based on at least one selected from a group consisting of: distances to valley locations having minimum bone density values, distances to teeth, and a preset reference bone density value.

11. The apparatus of claim 8, wherein the processor further configured to:
   determine whether each of the bone density values on the first rectilinear line is larger than a predetermined reference bone density value;
   set, if every one of the bone density values on the first rectilinear line is equal to or smaller than a preset reference bone density value, a fourth location and a fifth location that are used to generate a second rectilinear line and a third rectilinear line respectively;
   wherein the generation unit generate the second rectilinear line including the first location and the fourth location and the third rectilinear line including the first location and the fifth location;
   wherein the computation unit compute bone density values on locations of the alveolar bone on the generated second and third rectilinear lines using the medical image; and
   determine locations of the alveolar bone at which a second fastener and a third fastener to be inserted based on the computed bone density values on the second rectilinear line and the third rectilinear line.

* * * * *